US011426486B2

(12) United States Patent
Marteinsson et al.

(10) Patent No.: US 11,426,486 B2
(45) Date of Patent: Aug. 30, 2022

(54) CHITOSAN-CONTAINING FORMULATIONS (71) Applicant: Primex EHF., Siglufjordur (IS)

(72) Inventors: Rúnar Marteinsson, Siglufjordur (IS); Hélène L. Lauzon, Reykjavik (IS); Sigrídur Vigdís Vigfúsdóttir, Siglufjordur (IS)

(73) Assignee: Primex EHF., Siglufjordur (IS)

( * ) Notice: Subject to any disclaimer, the term of this patent is extended or adjusted under 35 U.S.C. 154(b) by 0 days.

(21) Appl. No.: 15/867,420

(22) Filed: Jan. 10, 2018

(65) Prior Publication Data
US 2018/0296724 A1    Oct. 18, 2018

Related U.S. Application Data (60) Provisional application No. 62/446,108, filed on Jan. 13, 2017.

(51) Int. Cl.
| | | |
|---|---|---|
| *A61L 26/00* | (2006.01) | |
| *A61P 17/02* | (2006.01) | |
| *A61K 47/12* | (2006.01) | |
| *A61K 31/722* | (2006.01) | |
| *A61K 45/06* | (2006.01) | |
| *A61K 9/06* | (2006.01) | |
| *A61K 9/00* | (2006.01) | |
| *A23L 3/3526* | (2006.01) | |
| *A23L 33/10* | (2016.01) | |
| *C08L 5/08* | (2006.01) | |

(52) U.S. Cl.
CPC ......... *A61L 26/0023* (2013.01); *A23L 3/3526* (2013.01); *A23L 33/10* (2016.08); *A61K 9/0014* (2013.01); *A61K 9/06* (2013.01); *A61K 31/722* (2013.01); *A61K 45/06* (2013.01); *A61K 47/12* (2013.01); *A61L 26/008* (2013.01); *A61L 26/009* (2013.01); *A61L 26/0066* (2013.01); *A61P 17/02* (2018.01); *C08L 5/08* (2013.01); *A61L 2300/404* (2013.01); *A61L 2300/41* (2013.01); *A61L 2300/604* (2013.01); *A61L 2430/34* (2013.01); *C08L 2201/54* (2013.01); *C08L 2203/02* (2013.01); *C08L 2203/20* (2013.01)

(58) Field of Classification Search
CPC . A61L 26/0023; A61L 26/0066; A61L 26/008
See application file for complete search history.

(56) References Cited

FOREIGN PATENT DOCUMENTS

| | | |
|---|---|---|
| CN | 102670929 | 9/2012 |
| CN | 102824308 | 12/2012 |
| EP | 2473200 | 9/2016 |
| JP | 01256375 | 4/1988 |
| WO | 2008156250 | 12/2008 |
| WO | 2010109433 | 9/2010 |
| WO | 2014126370 | 8/2014 |

OTHER PUBLICATIONS

FDA (Water for Pharmaceutical Use; Dec. 31, 1986; pp. 1-5).*
Natural Humectant (https://goatmilkstuff.com/blogs/goat-milk-soap/what-is-natural-humectant; downloaded on Nov. 5, 2020, pp. 1-12).*
Giuliano (Pharmaceutics, 2018, 10(3): 159, pp. 1-26).*
Drugbank (https://go.drugbank.com/drugs/DB11063 :downloaded on Jan. 27, 2022).*
Cho et al., "Water-soluble chitin as a wound healing accelerator", Biomaterials 20(22), 1999, 2139-2145.
PCT/IB2018/050155, "International Search Report and Written Opinion", dated Apr. 5, 2018, 12 pages.
Carlo Anchisi et al., "Physical properties of chitosan dispersions in glycolic acid", Il Farmaco, vol. 59, May 28, 2004, pp. 557-561.
Xiaoying Lu et al., "A proteomics study to explore the role of adsorbed serum proteins for PC12 cell adhesion and growth on chitosan and collagen/chitosan surfaces", Regenerative Biomaterials, 2018, pp. 261-273.
V.K. Mourya et al., "Chitosan-modifications and applications: Opportunities galore", Reactive & Functional Polymers 68, vol. 68, Mar. 13, 2008, pp. 1013-1051.
C.K.S. Pillai et al., "Chitin and chitosan polymers: Chemistry, solubility and fiber formation", Progress in Polymer Science, vol. 34, Apr. 11, 2009, pp. 641-678.
Marguerite Rinaudo et al., "Chitin and chitosan: Properties and applications", Progress in Polymer Science, vol. 31, Jun. 13, 2006, pp. 603-632.
Motohiko Sano et al., "Relationship between Solubility of Chitosan in Alcoholic Solution and Its Gelation", vol. 47 (7), Apr. 13, 1999, pp. 1044-1046.
A. Tolaimate et al., "Contribution to the preparation ofchitins and chitosans with controlled physico-chemical properties", Polymer, vol. 44, Oct. 6, 2003, pp. 7939-7952.

* cited by examiner

*Primary Examiner* — Pancham Bakshi
(74) *Attorney, Agent, or Firm* — Kilpatrick Townsend & Stockton, LLP; Jennifer Blackburn (57) ABSTRACT

Provided herein are chitosan-containing formulations, methods of making such formulations, and methods of using such formulations. Chitosan contemplated for use herein is preferably of high quality and its source is preferably of crustacean origin. The formulations contemplated herein are aqueous, either liquid- or viscous-like, varying in concentration and type of chitosan and acid used, and may include other components. Their uses are diverse, for oral/dental administration or topical/surface application to subjects (e.g. humans or animals) in need thereof or even food commodities, aiming to maintain a good condition where it is applied or contributing to health enhancement, healing, disease prevention or treatment. The present invention also relates to concentrated solutions that may be used for the formulation of other products.

9 Claims, 5 Drawing Sheets

CHITOSAN-CONTAINING FORMULATIONS

TECHNICAL FIELD

The present disclosure relates to chitosan-containing formulations, methods of making such formulations, and methods of using such formulations.

BACKGROUND

The information provided herein and references cited are provided solely to assist the understanding of the reader, and does not constitute an admission that any of the references or information is prior art to the present invention.

Chitin is a readily available biological material obtained from invertebrate skeletons as well as fungal cell walls. It is a linear 1,4-beta linked polymer composed of N-acetyl-D-glucosamine residues. Chitin (and its partially deacetylated form, chitosan) are biocompatible, biodegradable, nontoxic, antimicrobial and hydrating agents. Due to these properties, their applications are numerous in various fields. Chitin with a degree of deacetylation (DDA) >50% is considered as chitosan. Chitin is insoluble in most organic solvents while chitosan is soluble in dilute acidic solutions below pH 6.0. The main parameters influencing the characteristics of chitosan are its molecular weight (MW) and its DDA. Due to the diversity of the sources of chitosan, and to the fact that it is commercially available with a wide range of DDA and MW, each of which may affect chitosan properties, it is important to consider how these parameters may contribute to its bioactivity to optimize the desired application.

Solubilization of chitosan in a mild acid will render possible its use for different applications and contribute to its bioactivity, which mainly relies on the physical interaction between this cationic molecule and the negative charne of the other component(s) being attracted thereto. In certain environments where lysozyme is present (e.g., in biological fluids and tissues of many living organisms such as bacteria, plants, insects, birds, mammals, and the like), e.g. on skin, or in tears, saliva or mucous, depolymerization of chitosan will take place to release chit oligosaccharides and eventually NT-acetylglucosamine and glucosamine. In fact, a low DDA chitosan molecule tends to depolymerize faster than its high DDA counterpart (Cho et al. (1999) Biomaterials 20, 2139). Advantage can be taken of this property in the design of chitosan-containing products aiming to target specific applications.

SUMMARY

In accordance with the present disclosure, there are provided chitosan-containing formulations, methods of making such formulations, and methods of using such formulations.

In certain aspects and embodiments, the formulations of the present disclosure comprise:
chitosan,
at least one acid,
deionized water, and optionally
at least one polyol,
wherein said aqueous chitosan-containing formulations are suitable for administration to a subject in need thereof.

In some aspects, formulations contemplated herein comprise 0.1-10 wt % chitosan.

In certain aspects and embodiments, the formulations of the present disclosure consist essentially of:
chitosan,
at least one acid,
deionized water, and optionally
at least one polyol,
wherein said aqueous chitosan-containing formulations are suitable for administration to a subject in need thereof.

In some aspects, formulations contemplated herein contain in the range of about 0.1-10 wt % chitosan.

In some embodiments of the aspects and embodiments described herein, the formulation includes a polyol.

In some aspects, the present disclosure contemplates methods for making the above-described formulations, said methods comprising mixing chitosan with an amount of acidified deionised water effective to solubilize said chitosan.

In some aspects, the present disclosure contemplates methods for making aqueous chitosan-containing formulations having a Brookfield rotational viscosity of about 5 cps to 750 cps resulting in a homogeneous, easily sprayable solution, said methods comprising:
mixing a defined chitosan material with an amount of acidified deionised water effective to solubilize said chitosan;
solubilising said chitosan; and
optionally sterilizing and/or clarifying the resulting composition before packaging.

In some aspects, the present disclosure contemplates methods for making chitosan solutions having a Brookfield rotational viscosity in the range of about 1000 cps up to about 20,000,000 cps, or about 2000 cps up to about 20,000,000 cps, resulting in a homogeneous gel-like product, said methods comprising:
mixing a defined chitosan material with an amount of acidified deionised water effective to solubilize said chitosan;
solubilising said chitosan; and
optionally filtering; and
optionally sterilizing the resulting composition before packaging.

In some aspects, the instant disclosure further provides methods for treating or preventing diseases or disorders, or for maintaining a healthy or good condition, or the like, for example by local administration of the formulations as described herein. For example, in some embodiments, the disclosure provides methods of treating an external wound, the method comprising: topically administering to an external wound of a subject the compositions of any of the foregoing aspects (or any embodiments thereof). As another example, the disclosure provides methods of treating an external burn, the method comprising: topically administering to an external burn of a subject the compositions of any of the foregoing aspects (or any embodiments thereof). As another example, the disclosure provides methods of treating aches and pains, the method comprising: topically administering to a skin area of a subject the compositions of any of the foregoing aspects (or any embodiments thereof), wherein the skin area is proximate to (e.g., immediately above) the ache or pain. As another example, the disclosure provides methods of promoting gum health (e.g., by inhibiting the growth of oral bacteria), the method comprising: orally administering to a subject the compositions of any of the foregoing aspects (or any embodiments thereof). As another example, the disclosure provides methods of treating peri-implantitis, the method comprising: orally or dentally administering to a subject the compositions of any of the foregoing aspects (or any embodiments thereof).

A patient or subject to be treated by any of the compositions or methods of the present disclosure can mean either a human or a non-human animal. In an embodiment, the present disclosure provides methods for the treatment of a disease in a human patient in need thereof. In an embodiment, the present disclosure provides methods for the treatment of an inflammatory disease in a human patient in need thereof. In another embodiment, the present disclosure provides methods for the treatment of a disease in a veterinary patient in need thereof, including, but not limited to dogs, horses, cats, rabbits, gerbils, hamsters, rodents, birds, aquatic mammals, cattle, pigs, camelids, and other zoological animals.

In some embodiments of the compositions and methods disclosed herein, the formulation may further comprise one or more additional active ingredients, e.g., active agents selected from the group consisting of a steroid (such as a corticosteroid), and the like. In some embodiments the additional active agent includes an antibiotic, for example one or more antibiotics selected from the group consisting of azythromycin, ciprofloxacin, ofloxacin, gatifloxacin, levofloxacin, moxifloxacin, besifloxacin, and levofloxacin. In some embodiments, the additional active agent includes an antibiotic, for example one or more antibiotics selected from the group consisting of azythromycin, ciprofloxacin, ofloxacin, gatifloxacin, levofloxacin, moxifloxacin, besifloxacin, and levofloxacin. In some embodiments, the active agent includes two or more active agents and one of said active agents is an antiviral, for example one or more antivirals selected from the group consisting of ganciclovir, trifluridine, acyclovir, famciclovir, valacyclovir, penciclovir and cidofovir. In some embodiments, the active agent includes two or more active agents and one of the active agents is an antiviral, for example one or more antivirals selected from the group consisting of ganciclovir, trifluridine, acyclovir, famciclovir, valacyclovir, penciclovir and cidofovir.

The term "treating" refers to: preventing a disease, disorder or condition from occurring in a cell, a tissue, a system, animal or human which may be predisposed to the disease, disorder and/or condition but has not yet been diagnosed as having it; stabilizing a disease, disorder or condition, i.e., arresting its development; and/or relieving one or more symptoms of the disease, disorder or condition, i.e., causing regression of the disease, disorder and/or condition.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

Accordingly, in some aspects and embodiments of the present disclosure, there are provided methods of treating or preventing a disease or condition, that includes locally administering a formulation of any of the aspects or embodiments as disclosed herein.

DETAILED DESCRIPTION

Figure 1:
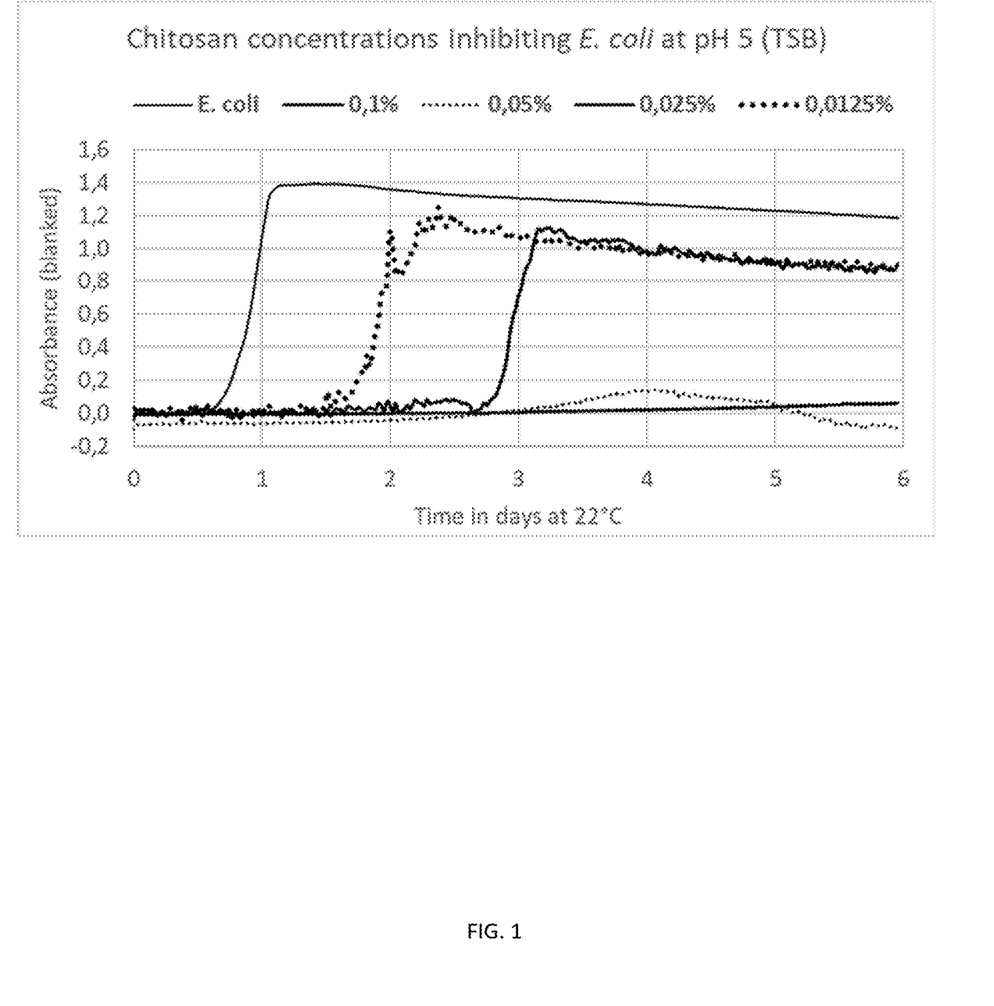
FIG. 1 demonstrates the antibacterial properties of chitosan acetate solutions as influenced by concentrations (% w/w) at pH 5 in Tryptic Soy Broth (TSB) against *E. coli* ATCC 8739. This reflects the ability of chitosan to be used as a natural preservative (biopreservative) or act as an active compound by its antibacterial action in different applications.
Figure 2:
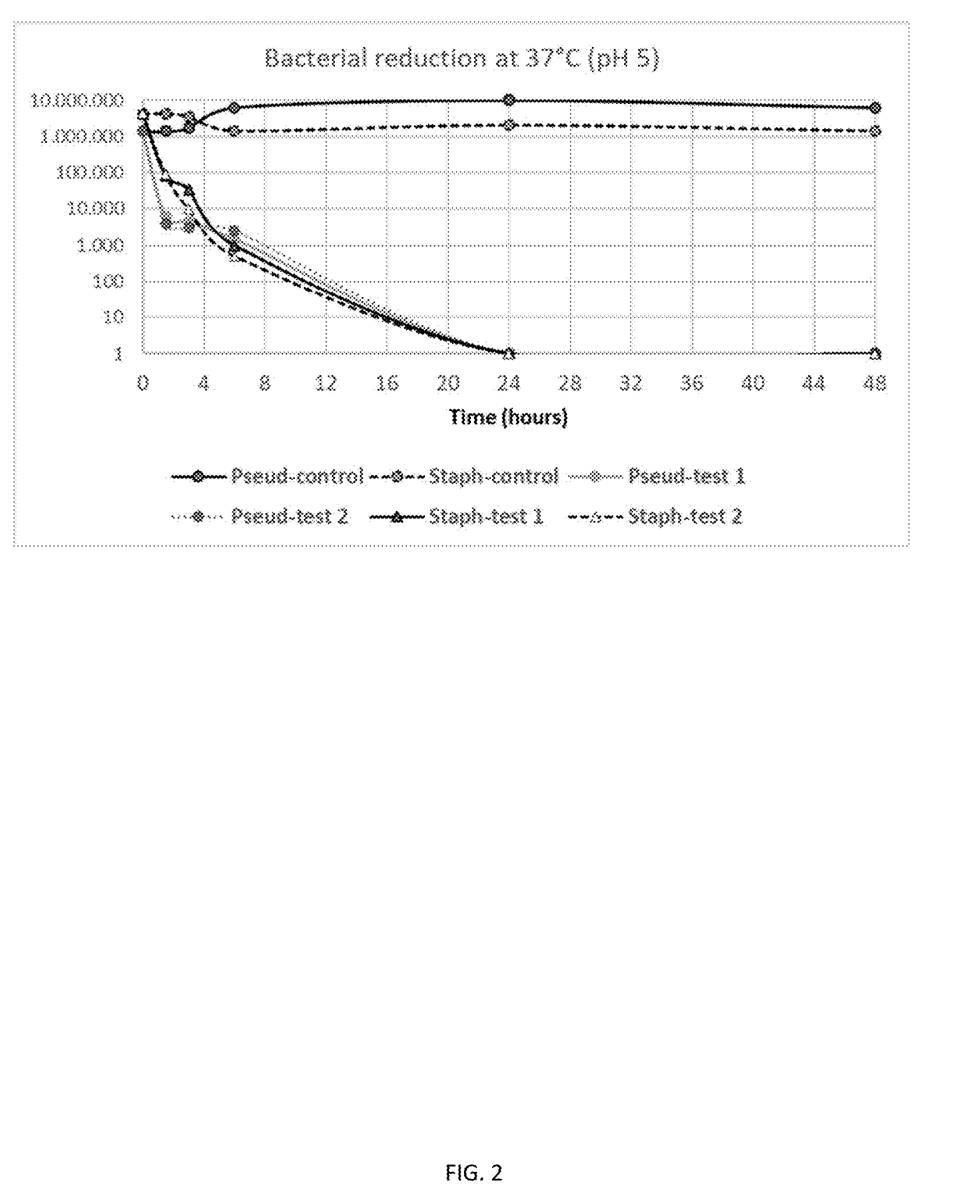
FIG. 2 presents the antibacterial activity of 0.65% (w/w) chitosan lactate solution against two skin pathogens, *Pseudomonas aeruginosa* ATCC 9027 ($1.4 \times 10^6$ cfu/ml) and *Staphylococcus aureus* ATCC 6538 ($4.3 \times 10^6$ cfu/ml), in duplicate (tests 1 and 2) at pH 5 in saline peptone water (37° C.). Detection limit: 1 cfu/ml indicates here not detected (<1 cfu/ml).
Figure 3:
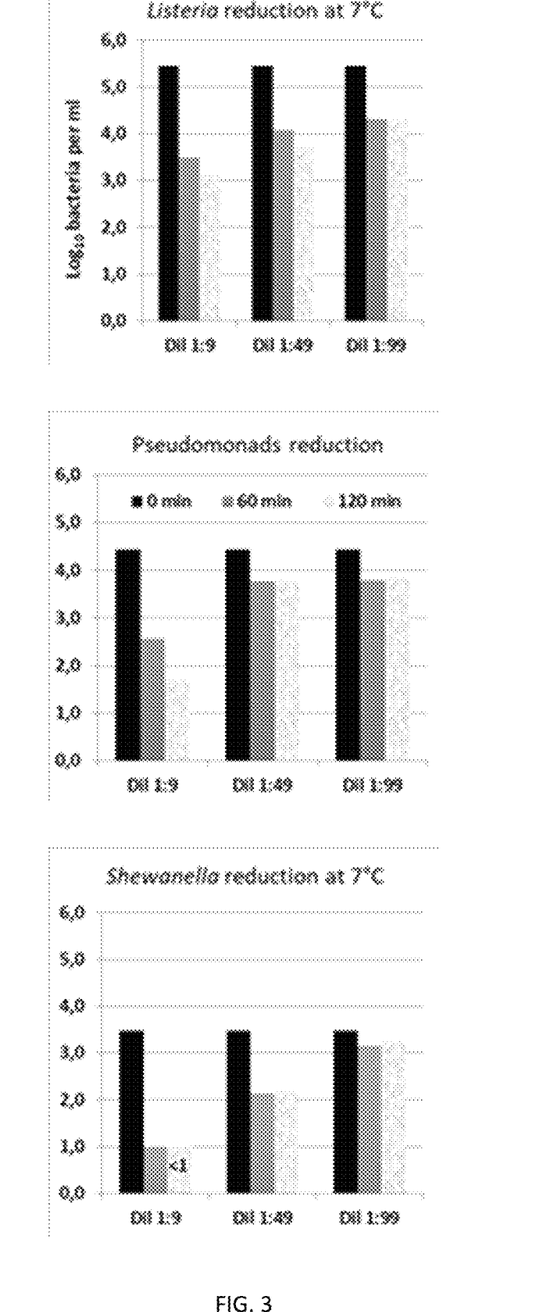
FIG. 3 summarizes an in vitro study on the effect of treatment time (0-60-120 min) and of dilution (dil 10×-50×-100×) of a chitosan acetate rinsing solution to reduce fish bacterial surface contamination. The diluting medium was a salmon flesh extract prepared by heating (1 fish: 9 water), autoclaving (15 min at 121° C.) and filtration prior to inoculation with fish bacterial strains: *Listeria monocytogenes, Pseudomonas* spp. and *Shewanella putrefaciens*. Effects: 2-log (dil 10×) and 1-log (dil 50×) drop after 60 min.
Figure 4:
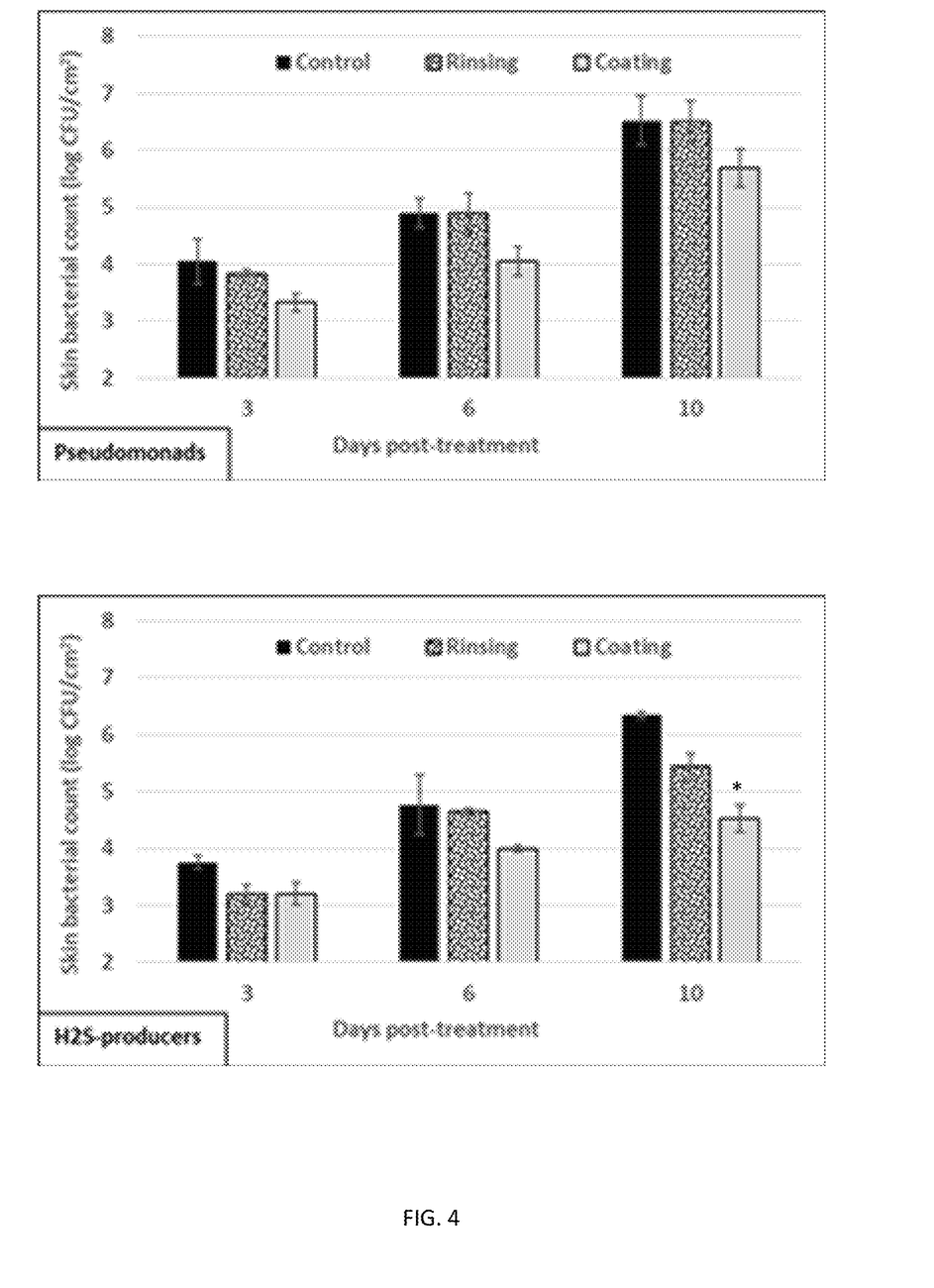
FIG. 4 summarizes the study on the effect of treatment type (control, chitosan rinsing or coating) on proliferation of spoilage bacteria (pseudomonads and $H_2S$-producing bacteria) on skin of whole, gutted cod (duplicate samples) during ice storage post-treatment. Results: Chitosan coating is more effective than rinsing treatment in retarding growth of fish spoilage bacteria. $H_2S$-producing bacteria are more sensitive to chitosan treatments than pseudomonads. Asterisk indicates count is significantly lower than control ($p<0.05$).
Figure 5:
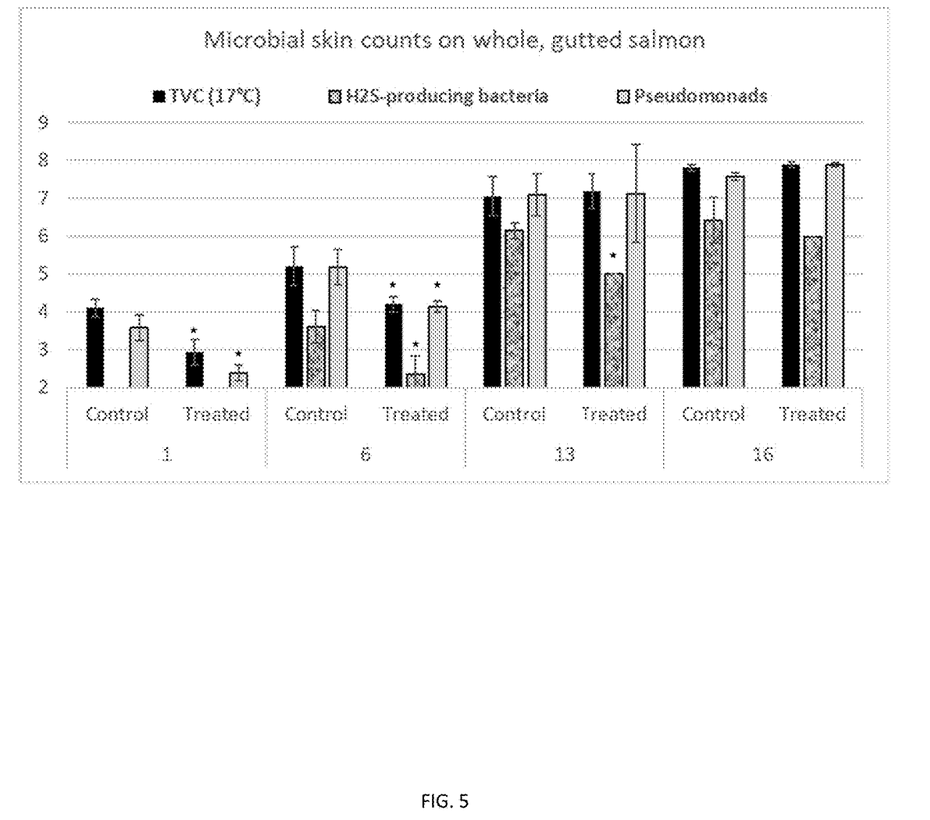
FIG. 5 summarizes the study on the effect of chitosan rinsing on microbial proliferation on skin of whole, gutted salmon (duplicate samples) during 16-day ice storage. Results: $H_2S$-producing bacteria are more sensitive to chitosan treatments than pseudomonads. The rinsing treatment slowed down the sensitive spoilage bacteria for at least 13 days. Asterisk indicates count is significantly lower than control ($p<0.05$).

In accordance with the present invention, there are provided aqueous chitosan-containing formulations comprising:
 chitosan,
 an amount of at least one acid effective to enhance the solubility of said chitosan in deionized water, and
 an amount of deionized water effective, in the presence of said acid, to solubilize said chitosan,
wherein said aqueous chitosan-containing formulations are suitable for administration (e.g., oral administration, dental or topical application) to a subject in need thereof (e.g., humans, farm animals and domesticated animals).

In accordance with some aspects and embodiments of the present invention, there are provided aqueous chitosan-containing formulations consisting essentially of:
 chitosan,
 an amount of at least one acid effective to enhance the solubility of said chitosan in deionized water, and
 an amount of deionized water effective, in the presence of said acid, to solubilize said chitosan,
wherein said aqueous chitosan-containing formulations are suitable for administration (e.g., oral administration, dental or topical application) to a subject in need thereof (e.g., humans, farm animals and domesticated animals).

Chitosan contemplated for use herein can be characterized in a variety of ways. For example, 1% of chitosan on a dry basis, in 1% acetic acid, may have a Brookfield rotational viscosity at 25° C. from about 5 cps to about 2,000,000 cps; in some embodiments, chitosan employed herein may have a Brookfield rotational viscosity at 25° C. from about 5 cps-10,000 cps; in some embodiments, chitosan employed herein may have a Brookfield rotational viscosity at 25° C. from about 5 cps-50,000 cps; in some embodiments, chitosan employed herein may have a Brookfield rotational viscosity at 25° C. from about 5 cps-100,000 cps; in some embodiments, chitosan employed herein may have a Brookfield rotational viscosity at 25° C. from about 5 cps-200,000 cps; in some embodiments, chitosan employed herein may have a Brookfield rotational viscosity at 25° C. from about 5 cps-300,000 cps; in some embodiments, chitosan employed herein may have a Brookfield rotational viscosity at 25° C. from about 5 cps-400,000 cps; in some embodiments, chitosan employed herein may have a Brookfield rotational viscosity at 25° C. from about 5 cps-500,000 cps; in some embodiments, chitosan employed herein may have a Brookfield rotational viscosity at 25° C. from about 5 cps-600,000 cps; in some embodiments, chitosan employed herein may have a Brookfield rotational viscosity at 25° C. from about 5 cps-700,000 cps; in some embodiments, chitosan employed herein may have a Brookfield rotational viscosity at 25° C. from about 5 cps-800,000 cps; in some embodiments, chitosan employed herein may have a Brookfield rotational viscosity at 25° C. from about 5 cps-900,000 cps; in some embodiments, chitosan employed herein may have a Brookfield rotational viscosity at 25° C. from about 5 cps-1,000,000 cps; in some embodiments, chitosan employed herein may have a Brookfield rotational viscosity at 25° C. from about 5 cps-1,100,000 cps; in some embodiments, chitosan employed herein may have a Brookfield rotational viscosity at 25° C. from about 5 cps-1,200,000 cps; in some embodiments, chitosan employed herein may have a Brookfield rotational viscosity at 25° C. from about 5 cps-1,300,000 cps; in some embodiments, chitosan employed herein may have a Brookfield rotational viscosity at 25° C. from about 5 cps-1,400,000 cps; in some embodiments, chitosan employed herein may have a Brookfield rotational viscosity at 25° C. from about 5 cps-1,500,000 cps; in some embodiments, chitosan employed herein may have a Brookfield rotational viscosity at 25° C. from about 5 cps-1,600,000 cps; in some embodiments, chitosan employed herein may have a Brookfield rotational viscosity at 25° C. from about 5 cps-1,700,000 cps; in some embodiments, chitosan employed herein may have a Brookfield rotational viscosity at 25° C. from about 5 cps-1,800,000 cps; in some embodiments, chitosan employed herein may have a Brookfield rotational viscosity at 25° C. from about 5 cps-1,900,000 cps; in some embodiments, chitosan employed herein may have a Brookfield rotational viscosity at 25° C. from about 5 cps-2,000,000 cps; and the like.

As used herein in connection with numerical values, the terms "approximately" and "about" mean +/−10% of the indicated value, including the indicated value.

As readily recognized by those of skill in the art, the amount of chitosan present in the formulations contemplated herein can vary widely, typically falling in the range of about 0.1% and about 10% by weight based on the weight of said formulation. In some embodiments, the chitosan concentration falls in the range of about 0.5-5%; in some embodiments, the chitosan concentration falls in the range of about 0.7-4%; in some embodiments, the chitosan concentration falls in the range of about 1-3%.

Chitosan materials contemplated for use herein can be further characterized by the percentage of deacetylation of said chitosan, which in some embodiments can be up to 100%; in some embodiments, the chitosan has a percentage of deacetylation from about 65 up to about 100%; in some embodiments, the chitosan has a percentage of deacetylation from about 70 up to about 100%; in some embodiments, the chitosan has a percentage of deacetylation from about 75 to about 100%; in some embodiments, the chitosan has a percentage of deacetylation from about 80 up to about 100%.

In some embodiments, chitosan contemplated for use herein is of any source of animal or microbial origin; in some embodiments, chitosan contemplated for use herein is of crustacean origin.

Chitosan materials contemplated for use herein can be further characterized with reference to one or more of the following:
a moisture content of <15%;
an ash content <1%,
a turbidity of <50 NTU,
a solubility of >99% and
<3 ppm heavy metals (i.e., As, Cd, Pb, Hg).

Chitosan materials which meet a plurality of the above-referenced criteria are also referred to herein as "high quality" chitosan.

As readily recognized by those of skill in the art, moisture content can be determined by a moisture analyser; ash content (on a dry basis) can be determined in a variety of ways, e.g., by dry ashing at 800° C. for 3 h, or similar method; turbidity can be determined by measuring turbidity of 1% chitosan (dry basis) in 1% acetic acid; and total heavy metals (As, Cd, Pb, Hg) can be determined by ICP/MS (USP730). Apparent viscosity of chitosan (1% w/w as dry basis) in 1% (v/w) acetic acid is evaluated at 25.0° C. according to ASTM F2103.

Deionised water contemplated for use herein typically comprises at least 80 wt % of the formulation.

Deionised water contemplated for use herein can be further characterized as USP purified water with total dissolved solids (TDS) <1 ppm, an electrical conductivity <1.3 µS/cm (@25° C.) and total organic carbon (TOC) <0.50 ppm.

In some embodiments of the present invention, the amount of acid effective to solubilize chitosan is at least about 10% percent of the weight of the chitosan with which the acid is mixed. In some embodiments of the present invention, the amount of acid effective to solubilize chitosan is at least about 20% percent of the weight of the chitosan with which the acid is mixed. In some embodiments of the present invention, the amount of acid effective to solubilize chitosan is at least about 30% percent of the weight of the chitosan with which the acid is mixed. In some embodiments of the present invention, the amount of acid effective to solubilize chitosan is at least about 40% percent of the weight of the chitosan with which the acid is mixed.

In some embodiments of the present invention, the acid effective to solubilize said chitosan comprises from about 40% up to 100% of the weight of the chitosan with which the acid is mixed.

In some embodiments, the acid contemplated for use herein is an organic acid. Exemplary organic acids include aliphatic or aromatic organic acid having in the range of about 2 up to 10 carbon atoms, such as, for example, glycolic acid, acetic acid, malic acid, citric acid, ascorbic acid, lactic acid, succinic acid, and the like, or a mixture of any two or more thereof.

In some embodiments, the acid contemplated for use herein is lactic acid.

In some embodiments, the acid contemplated for use herein is ascorbic acid.

In some embodiments, the acid contemplated for use herein is citric acid.

In some embodiments, the acid contemplated for use herein is malic acid.

In some embodiments, the acid contemplated for use herein is acetic acid.

In some embodiments, the acid contemplated for use herein is glycolic acid.

In some embodiments, the acid contemplated for use herein is succinic acid.

In some embodiments of the present invention, chitosan-containing formulations have a pH of <6. In some embodiments, such formulations have a pH in the range of about 3-5.9; in some embodiments, the formulations have a pH in the range of about 3.5-5.9; in some embodiments, the formulations have a pH in the range of about 4-5.9 in some embodiments, the formulations have a pH in the range of about 4.5-5.9; in some embodiments, the formulations have a pH in the range of about 5-5.9.

In some embodiments of the present invention, chitosan-containing formulations contemplated herein are substantially free of compounds that form insoluble complex(es) with chitosan, potentially inducing the precipitation thereof.

In some embodiments of the present invention, chitosan-containing formulations contemplated herein further comprise:
(i) one or more plasticizers (such as glycerol or other polyol) to favor a smooth, elastic and well performing seal on the skin;
(ii) one or more essential oils or plant extracts to enhance the inherent biological activity;
(iii) one or more iodophors to enhance the antimicrobial spectrum;
(iv) one or more preservatives and/or stabilisers to enhance product stability;
(v) honey; and/or
(vi) mixtures of any two or more thereof.

As used herein, the term "plasticizer" refers to a compound that modifies the physical properties of polymer chains, by changing their plasticity and viscosity in solution or in a product by reducing the interactions between segments of the polymer chains. As a result, softening is observed, as well as enhanced flexibility and decreased brittleness. Exemplary plasticizers contemplated for use herein include glycerol or other polyols.

Polyols contemplated for use herein typically have a molecular weight in the range of about 90-1000 g/mol; in some embodiments, the polyol has a molecular weight in the range of about 92-700 g/mol. Exemplary polyols include glycerol, PPG, PEG, maltitol, sorbitol, xylitol, and the like, as well as mixtures of any two or more thereof.

As used herein, the term "essential oil or plant extract" refers to the active agent(s) extracted from plants, as a concentrated hydrophobic liquid containing volatile aroma compounds that contribute to the characteristic fragrance (essence) of the oil or other active agent(s). Exemplary essential oils or plant extracts contemplated for use herein include essential oils or plant extracts of coriander, clove, caraway, cardamon, thyme, cinnamon, anise, sage, oregano, mint, peppermint, spearmint, basil, garlic, pine, lime, marigold, chamomile, eyebright, wood cranesbill, butternut root, juniper, lavender, common mallow, silverweed, rosemary, chickweed, stinging nettle, heartsease, bergamot, eucalyptus, neroli, lemon grass, almond, pomegranate, wild rose, mullein, damask rose, tea tree, and the like.

As used herein, the term "iodophor" refers to preparations containing iodine complexed with a solubilizing agent. Such preparations, e.g. povidone-iodine (PVP-I), iodine tincture and Lugol's iodine, are water-soluble and most effective under acidic conditions.

As used herein, the term "preservative" refers to a substance added to prevent decomposition by microbial growth or by undesirable chemical changes. Exemplary preservatives contemplated for use herein include sodium benzoate, benzyl alcohol with/without EDTA, benzalkonium chloride, chlorhexidine, Cosmocil® CQ, Dowicil®200, and the like.

As used herein, the term "stabiliser" refers to a substance added to prevent unwanted changes in a formulation and maintain proper shelf life. Exemplary stabilizers contemplated for use herein include oleic acid, lecithin, polysorbates, natural gums, or commercial mixed products including some of those compounds.

Chitosan-containing formulations contemplated herein can be used in a variety of ways, e.g., for the targeted treatment of wounds, aches and pains, skin inflammation due to insect bites, bedsores, ulcers, and the like.

In accordance with another embodiment of the present invention, there are provided aqueous chitosan-containing formulations comprising:
chitosan,
an amount of at least one acid effective to enhance the solubility of said chitosan in deionized water,
an amount of deionized water effective, in the presence of said acid, to solubilize said chitosan, and
at least one polyol.

In accordance with another embodiment of the present invention, there are provided aqueous chitosan-containing formulations consisting essentially of:
chitosan,
an amount of at least one acid effective to enhance the solubility of said chitosan in deionized water,
an amount of deionized water effective, in the presence of said acid, to solubilize said chitosan, and
at least one polyol.

Polyols contemplated for use herein typically have a molecular weight in the range of about 90-1000 g/mol; in some embodiments, the polyol has a molecular weight in the range of about 92-700 g/mol. Exemplary polyols include glycerol, PPG, PEG, maltitol, sorbitol, xylitol, and the like, as well as mixtures of any two or more thereof.

As readily recognized by those of skill in the art, the concentration of polyol can vary widely. For example, in some embodiments, the concentration of said polyol falls in the range of about 0.1-10%; in some embodiments, the concentration of said polyol falls in the range of about 0.5-10%; in some embodiments, the concentration of said polyol falls in the range of about 1-5% (w/w) of said formulation.

In accordance with another embodiment of the present invention, there are provided methods of producing aqueous chitosan-containing formulations, said method comprising mixing chitosan with an amount of acidified deionised water effective to solubilize said chitosan.

In accordance with yet another embodiment of the present invention, there are provided methods of producing aqueous chitosan-containing formulations having a Brookfield rotational viscosity of about 5 cps to 750 cps resulting in a homogeneous, easily sprayable solution, said method comprising:
mixing about 0.5% up to about 10% chitosan with an amount of acidified deionised water effective to solubilize said chitosan, wherein said chitosan has:
a weight-average molecular weight of from about 20,000 Daltons to about 500,000 Daltons;
an apparent viscosity of at least about 5 cps, and
a percentage of deacetylation of about 70% to 100%;
solubilising said chitosan for at least 30 minutes at 60° C.;
and optionally sterilizing and/or clarifying the resulting composition before packaging.

In some embodiments of the present invention, clarification of the resulting chitosan-containing solutions is accomplished by filtering through at least 30-micron filters.

In some embodiments of the present invention, sterilization of the resulting chitosan-containing solutions is accomplished by heating or irradiation.

In some embodiments of the present invention, chitosan-containing formulations contemplated herein may be prepared as basic formulations suitable for such uses as cosmetic and/or personal care applications to:
(i) cover and protect as a film-forming ingredient to favour moisture control;
(ii) provide antimicrobial activity as a natural preservative; and/or
(iii) act as a carrier of other active ingredients for slow release, due to ionic bonding to compounds and chitosan degradation by natural skin enzymes.

In some embodiments of the present invention, there are provided chitosan-containing formulations prepared by any of the methods described herein.

In accordance with still another embodiment of the present invention, there are provided methods of producing chitosan solutions having a Brookfield rotational viscosity in the range of about 1000 cps up to about 20,000,000 cps, or about 2000 cps up to about 20,000,000 cps, resulting in a homogeneous gel-like product, said method comprising:
mixing about 0.5% up to about 5% chitosan with an amount of acidified deionised water effective to solubilize said chitosan,
wherein said chitosan has
a weight-average molecular weight of from about 200,000 Daltons to about 2,000,000 Daltons;
an apparent viscosity of at least about 100 cps and
a percentage of deacetylation of from about 70% to 100%;
solubilising said chitosan for at least 30 minutes at 60° C., and
optionally filtering through at least 30-micron filters, and
optionally sterilizing the resulting composition before packaging.

The resulting homogeneous chitosan gel-like formulations may be applied in a variety of ways, for example, to:
(i) cover, seal and/or protect a wound or injured/inflammed skin or area;
(ii) result in a smooth and tailor-made film, easily shaped to the skin or area under treatment, that may be degraded by skin enzyme(s);
(iii) provide the appropriate conditions for moisture control;
(iv) control skin and wound infections;
(v) reduce itching and inflammation;
(vi) contribute to rapid healing; and/or
(vii) reduce hypertrophic scar formation;
(viii) relieve aches and pains related to sore muscles and joints; and/or
(ix) treat disorders within the oral mucosa and tooth supporting tissues.

Additional uses contemplated herein include the targeted cleaning of dirty wounds, udder care for milking animals, treatment of human and animal wounds or burns, to calm skin inflammation, relieve muscle aches and pains and/or to reduce itching due to insect bites or plant poison, sunburns, bedsores, ulcers, to promote oral health, e.g., by inhibiting the growth of oral bacteria, and to treat other disorders of the oral mucosa and the tooth-supporting tissues, and the like.

Homogeneous chitosan gel-like formulations contemplated herein have a variety of advantages, e.g., a gel will create a thicker film that lasts longer than a spray solution; such materials are less prone to rapid biodegradation, and can be more easily adapted to a wound than a bandage, just covering the area needed, tailor-made transparent and flexible "bandage" with various properties.

Additional formulations contemplated for use herein are fast-drying gels that are still flexible/elastic once applied onto the skin; such materials are beneficial for aching skin area and wound healing with reduced scar formation with respect to hypertrophic cicatrization, cutaneous lesions, chronic wounds, acute wounds, and the like.

In some embodiments of the present invention, there are provided chitosan-containing formulations prepared by any of the methods described herein.

In accordance with a further embodiment of the present invention, there are provided methods for treating a skin condition or damaged/aching area in a subject in need thereof, said method comprising applying an effective amount of a chitosan-containing formulation as described herein to the skin or area of said subject.

In accordance with still another embodiment of the present invention, there are provided methods for treating a skin condition in a subject in need thereof with chitosan, wherein the chitosan is applied in the form of a solution which may be applied by spraying or dipping to:
(i) help clean dirty wounds and contribute to rapid healing of humans and animals;
(ii) cover and protect superficial wounds (cuts, lacerations, grazes) or temporary skin defects/damage/irritation/inflammation and promote healing;
(iii) provide a sealing and protective barrier with antimicrobial properties and that maintains optimal moisture level;
(iv) reduce skin inflammation due to insect bites, plant poison, sunburns, bedsores, etc.;
(v) strengthen the skin natural protection and better withstand friction and related dryness;
(vi) promote natural microbiota of skin and reduce undesirable microorganisms; and/or
(vii) result in a smooth and tailor-made bandage-like film that will be degraded by skin enzyme(s), said method comprising applying, by spraying or dipping, an effective amount of a chitosan-containing solution as described herein to the skin of said subject.

In accordance with the present invention, there are provided methods for enhancing muscle, skin, dental, ear, eye and digestive health in animals and humans, said method comprising applying an effective amount of a chitosan-containing formulation as described herein.

In accordance with the present invention, there are provided methods of producing aqueous chitosan-containing solutions having a Brookfield rotational viscosity of about 50 cps to 50,000 cps resulting in a homogeneous, easily applicable solution, said method comprising:
mixing about 0.5% up to about 10% chitosan with an amount of acidified deionised water effective to solubilize said chitosan, wherein said chitosan has:
a weight-average molecular weight of from about one hundred thousand Daltons to about five hundred thousand Daltons;
an apparent viscosity of at least about 10 cps, and
a percentage of deacetylation of about 70% to 100%; or about 75-100%; or about 80-100%; or about 85-100%; or about 90-100%
solubilising said chitosan for at least 30 minutes at 60° C., and
optionally filtering through at least 30-micron filters, and optionally sterilizing the resulting composition before packaging.

The easily applicable solution contemplated herein could be the final concentration or a concentrate thereof, for dilution prior to application thereof.

In accordance with the present invention, there are provided methods for rinsing a perishable food commodity with chitosan prior to processing, wherein the chitosan is prepared in the form of a solution that may be diluted before application to:
 (i) achieve a reduction of the inherent surface contamination of the food commodity;
 (ii) reduce microbial transfer from the raw material to the processing equipment;
 (iii) better control the hygienic standard required during food processing; and/or
 (iv) promote quality and safety of the food processed, said method comprising applying the processing aid by rinsing the food commodity with an effective amount of a chitosan-containing solution as described herein.

In accordance with the present invention, there are provided methods for coating a perishable food commodity with chitosan, wherein the chitosan is prepared in the form of a solution that may be applied by spraying or dipping to:
 (i) help reduce inherent surface contamination of food commodity;
 (ii) cover and protect food commodity as long as necessary, hence reducing water loss and oxidative changes during storage time;
 (iii) provide an antimicrobial barrier to retard growth of spoilage and pathogenic microorganisms until removed by washing or deskinning or until degraded by surface enzymes; and/or
 (iv) extend the freshness period, thereby enhancing food quality as well as food safety,
said method comprising applying, by spraying or dipping, an effective amount of a chitosan-containing solution, as a processing aid, as described herein on a food commodity surface.

Additional Formulation Ingredients

The formulations of the present disclosure may also contain other components such as, but not limited to, additives, adjuvants, buffers, tonicity agents, bioadhesive polymers, and preservatives. It should be appreciated that the compositions of the present disclosure may be buffered by any common buffer system such as phosphate, borate, acetate, citrate, carbonate and borate-polyol complexes, with the pH and osmolality adjusted in accordance with well-known techniques to proper physiological values.

Tonicity agents include, for example, mannitol, sodium chloride, xylitol, etc. These tonicity agents may be used to adjust the osmolality of the compositions. In one aspect, the osmolality of the formulation is adjusted to be in the range of about 250 to about 350 mOsmol/kg. In a preferred aspect, the osmolality of the formulation is adjusted to between about 280 to about 300 mOsmol/kg.

An additive such as a sugar, a glycerol, and other sugar alcohols, can be included in the compositions of the present disclosure. Pharmaceutical additives can be added to increase the efficacy or potency of other ingredients in the composition. For example, a pharmaceutical additive can be added to a composition of the present disclosure to improve the stability of the active component thereof, to adjust the osmolality of the composition, to adjust the viscosity of the composition, or for another reason, such as effecting drug delivery. Non-limiting examples of pharmaceutical additives of the present disclosure include sugars, such as, trehalose, mannose, D-galactose, and lactose. In an embodiment, the sugars may be incorporated into a composition prior to hydrating the thin film (i.e., internally). In another embodiment, the sugars may be incorporated into a composition during the hydration step (i.e., externally).

In an embodiment, compositions of the present disclosure may further comprise one or more bioadhesive polymers in addition to chitosan. Bioadhesion refers to the ability of certain synthetic and biological macromolecules and hydrocolloids to adhere to biological tissues. Bioadhesion is a complex phenomenon, depending in part upon the properties of polymers, biological tissue, and the surrounding environment. Several factors have been found to contribute to a polymer's bioadhesive capacity: the presence of functional groups able to form hydrogen bridges (—OH, —COOH), sufficient elasticity for the polymeric chains to interpenetrate the mucous layer, and high molecular weight. Bioadhesion systems have been used in dentistry, orthopedics, ophthalmology, and in surgical applications. However, there has recently emerged significant interest in the use of bioadhesive materials in other areas such as soft tissue-based artificial replacements, and controlled release systems for local release of bioactive agents. Such applications include systems for release of drugs in the buccal or nasal cavity, and for intestinal or rectal administration.

In an embodiment, a composition of the present disclosure may include at least one bioadhesive polymer in addition to chitosan. The additional bioadhesive polymer can enhance the viscosity of the composition and thereby increase residence time at the site of treatment. Bioadhesive polymers of the present disclosure include, for example, carboxylic polymers like Carbopol® (carbomers), Noveon® (polycarbophils), cellulose derivatives including alkyl and hydroxyalkyl cellulose like methylcellulose, hydroxypropylcellulose, carboxymethylcellulose, gums like locust bean, xanthan, agarose, karaya, guar, and other polymers including but not limited to polyvinyl alcohol, polyvinyl pyrollidone, polyethylene glycol, Pluronic® (Poloxamers), tragacanth, and hyaluronic acid; phase-transition polymers for providing sustained and controlled delivery of enclosed medicaments (e.g., alginic acid, carrageenans (e.g., Eucheuma), xanthan and locust bean gum mixtures, pectins, cellulose acetate phthalate, alkylhydroxyalkyl cellulose and derivatives thereof, hydroxyalkylated polyacrylic acids and derivatives thereof, poloxamers and their derivatives, etc. Physical characteristics in these polymers can be mediated by changes in environmental factors such as ionic strength, pH, or temperature alone or in combination with other factors. In an embodiment, the optional one or more bioadhesive polymers is present in the composition from about 0.01 wt % to about 10 wt %/volume, preferably from about 0.1 to about 5 wt %/volume. In an embodiment, the compositions of the present disclosure further comprise at least one hydrophilic polymer excipient selected from, for example, PVP-K-30, PVP-K-90, HPMC, HEC, and polycarbophil. In an embodiment, the polymer excipient is selected from PVP-K-90, PVP-K-30 or HPMC. In an embodiment, the polymer excipient is selected from PVP-K-90 or PVP-K-30.

In an embodiment, if a preservative is desired, the compositions may optionally be preserved with any of many well-known preservatives, including sodium benzoate, benzyl alcohol with/without EDTA, benzalkonium chloride, chlorhexidine, Cosmocil® CQ, or Dowicil®200. In certain embodiments, it may be desirable for a formulation as described herein to not include any preservatives. In this regard, preservatives may in some embodiments not be necessary or desirable in formulations included in single use containers. In other embodiments it may be advantageous to include preservatives, such as in certain embodiments in which the formulations are included in a multiuse container.

Uses of Formulations

In certain aspects, the formulations disclosed herein may be used in a variety of ways, as disclosed above. In some embodiments, the disclosure provides methods of treating a wound, such as an external skin wound (e.g., an incision, a laceration, an abrasion, or a puncture), comprising topically administering any of the formulations disclosed herein to a subject at the site of the wound. In an analogous embodiment, the disclosure provides any of the formulations disclosed herein for use in treating a wound, such as an external skin wound (e.g., an incision, a laceration, an abrasion, or a puncture). In another analogous embodiment, the disclosure provides uses of any of the formulations disclosed herein for the manufacture of a medical device or medicament for treating a wound, such as an external skin wound (e.g., an incision, a laceration, an abrasion, or a puncture). Because the formulations disclosed herein are effective at controlling and/or inhibiting bacterial growth, such formulations are useful in inhibiting infection and allowing wounds to heal rapidly and/or effectively.

In some further embodiments, the disclosure provides methods of treating a burn, such as an external skin burn, comprising topically administering any of the formulations disclosed herein to a subject at the site of the burn. In an analogous embodiment, the disclosure provides any of the formulations disclosed herein for use in treating a burn, such as an external skin burn. In another analogous embodiment, the disclosure provides uses of any of the formulations disclosed herein for the manufacture of a medical device or medicament for treating a burn, such as an external skin burn. Because the formulations disclosed herein are effective at controlling and/or inhibiting bacterial growth, such formulations are useful in inhibiting infection and allowing burns to heal rapidly and/or effectively.

In the embodiments of the foregoing two paragraphs, the methods and uses may be carried out by topically administering the formulation to the site of the wound, e.g., topically administering the formulation to the site of the wound. This topical administration can be carried out by any suitable means. For example, in some embodiments, the formulations are applied to the skin surface using a finger or applicator. In some other embodiments, the formulation is disposed on a bandage, which is applied to the site of the wound. In some further such embodiments, the formulation is disposed on a bandage that smoothly conforms to the skin and is degradable, such as by skin enzymes.

In some other aspects related to the immediately foregoing aspects, the disclosure provides methods of reducing hypertrophic scar formation (e.g. resulting from a wound or a burn), comprising topically administering any of the formulations disclosed herein to a subject at the site of a wound or burn. In an analogous embodiment, the disclosure provides any of the formulations disclosed herein for use in reducing hypertrophic scar formation (e.g. resulting from a wound or a burn). In another analogous embodiment, the disclosure provides uses of any of the formulations disclosed herein for the manufacture of a medical device or medicament for reducing hypertrophic scar formation (e.g. resulting from a wound or a burn). As noted above, the formulations disclosed herein control and/or inhibit bacterial growth during wound and/or burn healing. Because poor healing of wound or burns is a contributing cause of hypertrophic scars, the formulations disclosed herein are useful for reducing the formation of such scars.

In some other aspects related to the immediately foregoing aspects, the disclosure provides methods of treating aches and pains, the method comprising: topically administering to a skin area of a subject the compositions of any of the foregoing aspects (or any embodiments thereof), wherein the skin area is proximate to (e.g., immediately above) the ache or pain (e.g., as perceived by the subject). In an analogous embodiment, the disclosure provides any of the formulations disclosed herein for use in treating an ache or pain. In another analogous embodiment, the disclosure provides uses of any of the formulations disclosed herein for the manufacture of a medical device or medicament for treating an ache or pain. The formulations disclosed herein reduce inflammation. Because inflammation is a contributing cause of aches and pains, the formulations disclosed herein are useful for treating aches and pains.

In some other aspects, the disclosure provides methods of promoting oral health (e.g. promoting gum health), comprising orally administering to a subject any of the formulations disclosed herein to the soft or hard tissues of the mouth. In an analogous embodiment, the disclosure provides any of the formulations disclosed herein for use in promoting oral health (e.g. promoting gum health). In another analogous embodiment, the disclosure provides uses of any of the formulations disclosed herein for the manufacture of a medical device or medicament for promoting oral health (e.g. promoting gum health).

In some other aspects related to the immediately foregoing aspect, the disclosure provides methods of treating disorders of the oral mucosa and/or the tooth supporting tissues, such as treating peri-implantitis, comprising orally administering to a subject any of the formulations disclosed herein. In an analogous embodiment, the disclosure provides any of the formulations disclosed herein for use in treating peri-implantitis. In another analogous embodiment, the disclosure provides uses of any of the formulations disclosed herein for the manufacture of a medical device or medicament for treating peri-implantitis.

In the embodiments of the foregoing two paragraphs, the methods and uses may be carried out by orally administering the formulation. This oral administration can be carried out by any suitable means. For example, in some embodiments, the formulations are orally administered via a mouthwash or other aqueous medium. In some other embodiments, the formulation is applied at the site of inflamed tissue of the mouth using an applicator, e.g., as a gel or other medium that does not easily wash away from the site of application. In some further such embodiments, the formulation is disposed on a sheet or device and the sheet or device is disposed at the site of inflamed tissue in the mouth.

EXAMPLES

The following examples are provided to further illustrate aspects of the invention. These examples are non-limiting and should not be construed as limiting any aspect of the invention.

Example 1

Preparation and Uses of Chitosan-Containing Formulations

Chitosan-containing formulations are prepared as follows on a per kg basis or with slight variations to reach the desired viscosity and acidity level:

mix 11.36 g lactic acid (88%) with 954.36 g deionised water, add 22.52 g chitosan powder (adjusted for a moisture content of 10.5%; 3000-9000 cps, 70-90% DDA) to solubilize said chitosan while heating the solution to 60° C. with stirring for at least 30 minutes The solution thus obtained is clarified through at least 30-micron filters before packaging.

Use as a Tailor-Made Transparent, Flexible Bandage

Example 1a

Treatment of Foot Injury with Chitosan Gel

Skin lacerated by accident on a child's big toe, resulting in an open area of 1.5×2 cm, along with minor wounds and scratches around it, was treated with a chitosan-containing formulation according to the present invention. Basic treatment (wound cleaning with dedicated agent and covered with a gauze, with daily renewal) was performed for 4 days, but with obvious formation of bacterial biofilm that was torn away with gauze removal causing further bleeding. From the fifth day, a chitosan gel was applied daily for 6 days as a layer to cover the wounded area, allowed to dry and covered with a gauze for the first day, and then a patch for the next two days. No bacterial growth was visible the next day, and a protective layer had formed. On the 7th day, a thin red skin had formed, with no obvious wound opening. Healing occurred rapidly thereafter and was completed one week post-treatment (PT), with no signs of the wound.

Example 1b

Treatment of a Second Degree Burn

A 3-year old child, accidentally burned on contact (on the left palm after placing its hand on a hot stove), was treated with a chitosan-containing formulation according to the present invention. Initial treatment at the hospital included application of a vaseline layer to maintain moisture and a covering patch. This was renewed 2 days later and repeated a few times until day 25 post-accident (PA). On that examination day, the superficial layer of skin was sloughing off and deeper injuries covered with crusts. There were also extensive areas with red inflammatory/granulation tissue.

The treatment with chitosan gel started 25 days PA by applying a gel layer on the wounded area. Four days later, the injury had developed a more normal skin colour, as the inflammatory zone had decreased, leaving smaller, demarcated areas of inflammation/granulation, and the crusts had reduced. At this time, the chitosan gel was reapplied and covered with a bandage. One month after the accident or 5 days post-chitosan treatment (PCT), the wound was reexamined, showing three demarcated areas with inflammation, and larger healing areas with skin colour approaching normal. Chitosan gel was applied again on days 5-7-9PCT. Seven days PCT, two demarcated areas were present with deeper injury, on the periphery of the original injury. Nine days PCT, the two deeper injuries were still healing, with scar tissue beginning to form. Twelve days PCT, deeper injuries had all healed with scar tissue, scars seen as redness and slight contracture of palmar skin.

Example 1c

Treatment after Surgery for Wound Healing and Hypertrophic Scar Reduction

Chitosan gel was applied to one of the two belly cuts resulting from a laparoscopic appendectomy. The longer upper cut was about 2 cm held closed with 2 stitches, while the lower and shorter cut (1 cm) at the pubic hairline only had one stitch. The upper cut was treated with the gel starting after the adhesive patch was removed, i.e. 5 days post-surgery (PS). Stitches were removed 10 days PS. Gel was applied almost daily, resulting in 125 gel applications during a 5-month period. Two months PS, half of the treated cut was healing faster, having mostly disappeared four months PS. At that time, the rest of the upper cut and the lower cut were still visible but had faded in appearance, getting more even with the skin. After five months PS, the untreated smaller cut had developed into a slightly hypertrophic scar (1 cm) while hypertrophy could not be seen on the treated area.

Example 2

Preparation and Uses of Additional Chitosan-Containing Formulations

Additional chitosan-containing formulations are prepared as follows on a per kg basis or with slight variations to reach the desired viscosity and acidity level:

mix 17.05 g lactic acid (88%) with 941.15 g deionised water, and add 30.04 g chitosan powder (adjusted for a moisture content of 13.5%; 4-40 cps, 75-90% DDA) slowly to solubilize said chitosan while heating the solution to 60° C. with stirring for at least 30 minutes, while adding 11.76 g glycerol (85%).

The solution thus obtained is clarified through at least 30-micron filters before packaging.

The prepared formulations are subjected to various tests such as evaluation of appearance, pH and viscosity.

Use as a Tailor-Made Transparent, Flexible Film to Calm Burnt Skin, Scratches and Wounds

Example 2a

Treatment of Skin Burnt or Irritated by Poisonous Plants

The sap of giant hogweeds spread over the hands, forearms and legs of an adult man during the plant removal without him noticing it. This happened during a sunny day in August. Five days later, burn-like lesions were visible on these areas, along with fluid-filled blisters. Treatment with chitosan gel or spray twice a day rapidly decreased blister formation, which had ceased the following day (6 days PA). The treatment was continued for 10 days, with successful healing, leaving a reddish or brownish tone on the skin at the most damaged areas.

Example 2b

Treatment of Sunburn

After the skin has been burnt by sun radiation, the spray can be applied as a thin layer to create a protective film, reduce inflammation and maintain skin moisture. Daily application is recommended until no longer needed.

Example 3

Preparation and Use of Additional Chitosan-Containing Formulations

Additional chitosan-containing formulations are prepared as follows on a per kg basis or with slight variations to reach the desired viscosity and acidity level:

mix 20.98 g glacial acetic acid with 979.02 g deionised water and add 50.00 g chitosan powder on a dry basis (10-100 cps, 75-85% DDA) slowly to solubilize the chitosan properly while gently heating the solution with stirring for at least 30 minutes.

The solution thus obtained is clarified through at least 30-micron filters before packaging.

The prepared formulations are subjected to various tests such as evaluation of appearance, pH and viscosity.

Upon use, the chitosan concentrate is diluted 50-fold into an ice-water slurry to rinse and chill whole fish properly for 20-30 min before bulk packaging. This will retard growth of fish spoilage bacteria for at least 3 days during ice-chilled storage.

Example 4

Preparation and Use of Additional Chitosan-Containing Formulations

Additional chitosan-containing formulations are prepared as follows on a per kg basis or with slight variations to reach the desired viscosity and acidity level:

mix 5.2 g glacial acetic acid with 972.5 g deionised water and add 15.0 g chitosan powder on a dry basis (300-750 cps, 75-85% DDA) slowly to solubilize it properly while gently heating the solution with stirring for at least 30 minutes, while adding 22.3 g glycerol (85%).

The solution thus obtained is clarified through at least 30-micron filters before packaging.

The prepared formulations are subjected to various tests such as evaluation of appearance, pH and viscosity.

Upon use, the chitosan solution is applied to whole fish by dipping or coating before bulk packaging. This will retard growth of fish spoilage bacteria for at least 3-4 days during ice-chilled storage.

The invention illustratively described herein may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

Other embodiments are set forth within the following claims.

What is claimed is:

1. An aqueous chitosan-containing a formulation consisting of
    (a) chitosan in a range of 0.1% to 10% by weight, based on the weight of the formulation;
    (b) at least one acid in an amount of at least 10% of the weight of the chitosan;
    (c) water in an amount of at least 80 wt % of the formulation;
    (d) a preservative; and
    (e) optionally one or more of a polyol having a molecular weight of 90-1000 g/mol, honey, or one or more essential oils.

2. The formulation of claim 1, wherein the formulation consists of
    (a) the chitosan;
    (b) the at least one acid;
    (c) the water;
    (d) the preservative;
    (e) a polyol having a molecular weight of 90-1000 g/mol;
    (f) optionally honey and/or one or more essential oils.

3. The formulation of claim 1, wherein the formulation consists of
    (a) the chitosan;
    (b) the at least one acid;
    (c) the water;
    (d) the preservative;
    (e) honey; and
    (f) optionally a polyol having a molecular weight of 90-1000 g/mol and/or one or more essential oils.

4. The formulation of claim 1, wherein the formulation consists of
    (a) the chitosan;
    (b) the at least one acid;
    (c) the water;
    (d) the preservative;
    (e) one or more essential oils; and
    (f) optionally a polyol having a molecular weight of 90-1000 g/mol and/or honey.

5. The formulation of claim 1, wherein a 1% solution of the chitosan on a dry basis, in 1% acetic acid, has a Brookfield rotational viscosity at 25° C. from 3000 cps to 9000 cps.

6. The formulation of claim 1, wherein the acid comprises an organic acid.

7. The formulation of claim 6, wherein the organic acid comprises glycolic acid, acetic acid, malic acid, citric acid, ascorbic acid, succinic acid, lactic acid, or a mixture thereof.

8. The formulation of claim 1, wherein the chitosan is present in a range of 1% to 3% by weight, based on the weight of the formulation.

9. The formulation of claim 1, wherein the chitosan has an average molecular weight of from about 200,000 Daltons to about 2,000,000 Daltons and an apparent viscosity of at least about 100 cps, and wherein the formulation has a Brookfield rotational viscosity in the range of about 1,000 cps to about 20,000,000 cps.

\* \* \* \* \*